(12) United States Patent  
Takahashi

(10) Patent No.: US 8,016,754 B2
(45) Date of Patent: Sep. 13, 2011

(54) ENDOSCOPE APPARATUS

(75) Inventor: Masaya Takahashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1269 days.

(21) Appl. No.: 11/584,906

(22) Filed: Oct. 23, 2006

(65) Prior Publication Data

US 2007/0100209 A1    May 3, 2007

(30) Foreign Application Priority Data

Oct. 31, 2005 (JP) .................................. 2005-316761
Jun. 22, 2006 (JP) .................................. 2006-172176
Aug. 11, 2006 (JP) .................................. 2006-220099

(51) Int. Cl.
*A61B 1/06* (2006.01)

(52) U.S. Cl. ....................................................... 600/167

(58) Field of Classification Search .................. 600/103, 600/129, 163, 167, 168, 173, 176
See application file for complete search history.

(56) References Cited

U.S. PATENT DOCUMENTS

| 4,777,524 | A  | * | 10/1988 | Nakajima et al. | ................ | 348/76 |
| 5,231,473 | A  | * | 7/1993 | Kawamura et al. | ............ | 359/694 |
| 5,531,664 | A  | * | 7/1996 | Adachi et al. | ................. | 600/149 |
| 6,117,071 | A  | * | 9/2000 | Ito et al. | ......................... | 600/168 |
| 6,185,375 | B1 | * | 2/2001 | Mikami | ........................... | 396/84 |
| 6,409,658 | B1 | * | 6/2002 | Mitsumori | ..................... | 600/167 |
| 6,413,207 | B1 | * | 7/2002 | Minami | ........................ | 600/109 |
| 6,447,447 | B1 | * | 9/2002 | Mitsumori | ..................... | 600/167 |
| 7,294,102 | B2 | * | 11/2007 | Jones et al. | .................... | 600/151 |
| 7,338,439 | B2 | * | 3/2008 | Kanai | ............................ | 600/176 |
| 2002/0016526 | A1 | * | 2/2002 | Akiba | ........................... | 600/167 |
| 2004/0097791 | A1 | * | 5/2004 | Tokuda et al. | ................. | 600/173 |
| 2008/0227060 | A1 | * | 9/2008 | Esashi et al. | ................... | 434/113 |

FOREIGN PATENT DOCUMENTS

JP        2004-129950        4/2004

* cited by examiner

*Primary Examiner* — Philip Smith
(74) *Attorney, Agent, or Firm* — Scully, Scott, Murphy & Presser, P.C.

(57) ABSTRACT

An endoscope apparatus includes a front end section which is rigid, and a flexible tube which has a bent portion. One end of a tube which can be bent is fixed to a lens barrel which holds an optical mechanism having a movable section. The tube is extended in a longitudinal direction of the flexible tube of the endoscope apparatus, and at least a part of a shape memory element is accommodated inside the tube. One end of the shape memory element is fixed to an end of the tube, which is not fixed to the lens barrel, and the other end of the shape memory element is mechanically connected to the movable section of the optical mechanism which includes the movable section. Due to expansion (elongation) and contraction of the shape memory element, relative positions of the movable section of the optical mechanism which includes the movable section, and one end of the tube fixed to the lens barrel are changed.

35 Claims, 22 Drawing Sheets

ENDOSCOPE APPARATUS

CROSS-REFERENCE TO RELATED APPLICATION

The present application is based upon and claims the benefit of priority from the prior Japanese Patent Applications No. 2005-316761 filed on Oct. 31, 2005, No. 2006-172176 filed on Jun. 22, 2006, and No. 2006-220099 filed on Aug. 11, 2006, the entire contents of which are incorporated herein by reference.

BACKGROUND OF THE INVENTION

1. Field of the Invention

The present invention relates to an endoscope apparatus, and particularly to an endoscope apparatus which includes a focusing mechanism.

2. Description of the Related Art

In an endoscope which includes an imaging unit at a front end section, and a flexible tube having a bent portion, normally, for observing an endoscope image in an optimum condition, it is necessary to perform focusing by moving a focusing lens and an imaging device. For this, an imaging apparatus for endoscope has been proposed in Japanese Patent Application Laid-open Publication No. 2004-129950. In the imaging apparatus for endoscope according to the Japanese Patent Application Laid-open Publication No. 2004-129950, inside a front end section of the endoscope, a shape memory alloy is used as a means for varying relative positions of an optical device and an imaging device.

In an endoscope apparatus disclosed in Japanese Patent Application Laid-open Publication No. 2004-129950, inside the front end section of the endoscope which is rigid, the relative positions of the optical device and the imaging device are changed by using the shape memory alloy. The endoscope is structured such that focusing is performed by changing the relative positions of the optical device and the imaging device.

However, an amount of change in the relative positions of the optical device and the imaging device is attributable to a length of the shape memory alloy which is included in the front end section of the endoscope, which is rigid. Since the rigid front end section of the endoscope cannot be made substantially long, from a point of view of functions of the endoscope, a length of the shape memory alloy inside the front end section of the endoscope is restricted. Therefore, in a structure according to a conventional technology, an increase in the amount of change in the relative positions of the optical device and the imaging device for focusing cannot be dealt with.

SUMMARY OF THE INVENTION

The present invention is made in view of the abovementioned issues, and an object of the present invention is to provide an endoscope apparatus which is capable of focusing by using a shape memory alloy, and increasing an amount of change in relative positions of an optical device and an imaging device for focusing, without increasing a diameter of a front end section of the endoscope.

To solve the abovementioned issues, and to achieve the object, according the present invention, it is possible to provide an endoscope apparatus including a front end section which is rigid, and which includes an optical mechanism which includes a movable section, and a flexible tube which has a bent portion.

One end of a tube member which can be bent, is fixed to a lens barrel which holds the optical mechanism which includes the movable section.

The tube member is extended in a longitudinal direction of the flexible tube which is included in the endoscope apparatus.

At least a part of a shape memory element is accommodated inside the tube member.

One end of the shape memory element is fixed to an end of the tube member which is not fixed to the lens barrel, and the other end of the shape memory element is mechanically connected to the movable section of the optical mechanism which includes the movable section.

Relative positions of the movable section of the optical mechanism which includes the movable section, and the end of the tube member which is fixed to the lens barrel, are changed by expansion and contraction of the shape memory element.

Moreover, according to a preferable aspect of the present invention, it is desirable that a bias-applying elastic body is disposed in the lens barrel such that a force is exerted in a reverse direction of changing the relative positions of the movable section of the optical mechanism which includes the movable section, and the end of the tube member which is fixed to the lens barrel, by a change in a length of the movable section of the optical mechanism which includes the movable section, by a phase transition of the shape memory element.

Furthermore, according to another preferable aspect of the present invention, it is desirable that one end of the shape memory element is mechanically connected to the movable section of the optical mechanism which includes the movable section, via a connecting section, and the movable section has a groove, and the connecting section is connected to the groove of the movable section via a gap between the connecting section and the groove.

According to still another preferable aspect of the present invention, it is desirable that a stopper for limiting a range of movement of the movable section of the optical mechanism which includes the movable section, is installed on the lens barrel.

Moreover, according to still another preferable aspect of the present invention, it is desirable that a buffering elastic body which exerts on the end of the tube member which fixes the end of the shape memory element, a force in a reverse direction of a force generated at a time of change in the length by the phase transition of the shape member element, is installed.

Furthermore, according to still another preferable aspect of the present invention, it is desirable that a spring constant of the buffering elastic body is greater than a spring constant of the bias-applying elastic body.

According to still another preferable aspect of the present invention, it is desirable that the buffering elastic body is disposed in the front end section which is rigid, which includes the optical mechanism which includes the movable section.

Moreover, according to still another preferable aspect of the present invention, it is desirable that the buffering elastic body and the shape memory element are connected electrically.

Furthermore, according to still another preferable aspect of the present invention, it is desirable that an axial direction of the buffering elastic body and an axial direction of the bias-applying elastic body are parallel, and at least a part of the buffering elastic body and a part of the bias-applying elastic body overlap by projecting in a vertical direction from the axial direction of the buffering elastic body.

According to still another preferable aspect of the present invention, it is desirable that one end of the shape memory element is fixed to the end of the tube member which is not fixed to the lens barrel, and the other end of the shape memory element is mechanically connected to the movable section of the optical mechanism which includes the movable section, via a buffering elastic body, and the relative positions of the movable section of the optical mechanism which includes the movable section, and the end of the tube member which is fixed to the lens barrel, are changed by expansion and contraction of the shape memory element, and excessive expansion and contraction of the shape memory element, beyond the change in the relative position, is absorbed by expansion and contraction of the buffering elastic body.

Moreover, according to still another preferable aspect of the present invention, it is desirable that a spring constant of the buffering elastic body is greater than a spring constant of the bias-applying elastic body.

Furthermore, according to still another preferable aspect of the present invention, it is desirable that the buffering elastic body is disposed in the front end section which is rigid, which includes the optical mechanism which includes the movable section.

According to still another preferable aspect of the present invention, it is desirable that the buffering elastic body and the shape memory element are connected electrically.

Moreover, according to still another preferable aspect of the present invention, it is desirable that an axial direction of the buffering elastic body and an axial direction of the bias-applying elastic body are parallel, and at least a part of the buffering elastic body and a part of the bias-applying elastic body overlap by projecting in a vertical direction from the axial direction of the buffering elastic body.

Furthermore, according to still another preferable aspect of the present invention, it is desirable that the shape memory element is connected upon bending at a portion at which the shape memory element is mechanically connected to the movable section of the optical mechanism which includes the movable section.

According to still another preferable aspect of the present invention, it is desirable that the tube member is non-conductive.

Moreover, according to still another preferable aspect of the present invention, it is desirable that the tube member is accommodated in a hollow cable member which has a high coefficient of elasticity, and one end of the hollow cable member having the high coefficient of elasticity on a side of the tube member which is not fixed to the lens barrel, and the shape memory element, are fixed.

Furthermore, according to still another preferable aspect of the present invention, it is desirable that the hollow cable member having the high coefficient of elasticity is a contact spring or a cable which includes a plurality of wires.

According to still another preferable aspect of the present invention, it is desirable that the tube member is thermally connected to a pipe conduit of an endoscope.

Moreover, according to still another preferable aspect of the present invention, it is desirable that the pipe conduit is one of a gas pipe conduit and a liquid pipe conduit.

Furthermore, according to still another preferable aspect of the present invention, it is desirable that the optical mechanism which includes the movable section, includes an imaging device, and not less than half a length of the shape memory element is disposed toward the flexible tube, farther than a position of the imaging device.

According to still another preferable aspect of the present invention, it is desirable that the movable section of the optical mechanism which includes the movable section, is an imaging device.

Moreover, according to still another preferable aspect of the present invention, it is desirable that one end of the shape memory element is fixed by one end of the tube member, and the other end of the tube member is not fixed to the lens barrel, and in the hollow cable member having the high coefficient of elasticity, one end of the hollow cable member having the high coefficient of elasticity, and one end of the shape memory element are fixed, and the other end of the hollow cable member having the high coefficient of elasticity is fixed to the lens barrel, and a force is exerted in a reverse direction of a force which is generated when a length is changed due to phase transition of the shape memory element, and a length is changed in the same direction as the direction of change in length by the phase transition of the shape memory element.

Furthermore, according the present invention, it is possible to provide an endoscope apparatus which includes a front end section which is rigid, and includes an optical mechanism including a movable section, and a flexible tube which has a bent portion.

One end of a hollow cable member which has a high coefficient of elasticity and which can be bent, is fixed to a lens barrel which holds the optical mechanism which includes the movable section.

The hollow cable member is extended in a longitudinal direction of the flexible tube of the endoscope apparatus, and at least apart of a shape memory element is accommodated inside the hollow cable member.

One end of the shape memory element is fixed to an end of the hollow cable member which is not fixed to the lens barrel, and the other end of the shape memory element is mechanically connected to the movable section of the optical mechanism which includes the movable section.

The endoscope apparatus further includes, an energizing means which energizes and heats up the shape memory element.

An insulation-coating process is performed on a portion other than a portion at which the shape memory element is electrically connected to the energizing means, and a temperature of the shape memory element is changed by heating by the energizing means (power supplying means).

Relative positions of the movable section of the optical mechanism which includes the movable section, and the end of the hollow cable member which is fixed to the lens barrel, are changed by expansion and contraction based on a temperature change of the shape memory element.

According to still another preferable aspect of the present invention, it is desirable that a bias-applying elastic body is disposed in the lens barrel such that a force is exerted in a reverse direction of changing the relative positions of the movable section of the optical mechanism which has the movable section, and the end of the hollow cable member which is fixed to the lens barrel, by a change in a length of the movable section of the optical mechanism which includes the movable section, by a phase transition of the shape memory element.

Moreover, according to still another preferable aspect of the present invention, it is desirable that one end of the shape memory element is mechanically connected to the movable section of the optical mechanism which includes the movable section, via a connecting section. The movable section has a groove, and the connecting section is connected to the groove of the movable section via a gap between the connecting section and the groove.

Furthermore, according to still another preferable aspect of the present invention, it is desirable that a stopper for limiting a range of movement of the movable section of the optical mechanism which includes the movable section, is installed on the lens barrel.

According to still another preferable aspect of the present invention, it is desirable that the shape memory element is connected upon bending at a portion at which the shape memory element is mechanically connected to the movable section of the optical mechanism which includes the movable section.

Moreover, according to still another preferable aspect of the present invention, it is desirable that the hollow cable member is a contact spring or a cable which includes a plurality of wires.

Furthermore, according to still another preferable aspect of the present invention, it is desirable that a force in a reverse direction of a force generated at a time of change in the length by the phase transition of the shape memory element, is exerted on the hollow cable member, and a length is changed in a direction same as the change in the length by the phase transition of the shape memory element.

According to still another preferable aspect of the present invention, it is desirable that the hollow cable member is thermally connected to a pipe conduit of an endoscope.

Moreover, according to still another preferable aspect of the present invention, it is desirable that the pipe conduit is one of a gas pipe conduit and a water pipe conduit.

Furthermore, according to still another preferable aspect of the present invention, it is desirable that the optical mechanism which includes the movable section, includes an imaging device, and not less than half a length of the shape memory element is disposed toward the flexible tube, farther than a position of the imaging device.

According to still another preferable aspect of the present invention, it is desirable that the movable section of the optical mechanism which includes the movable section, is an imaging device.

Moreover, according to still another preferable aspect of the present invention, it is desirable that a material in the insulation-coating process is parylene.

Furthermore, according to the present invention, it is possible to provide an endoscope apparatus including a front end section which is rigid, and which includes an optical mechanism which includes a movable section, and a flexible tube which has a bent portion.

A shape memory element is extended from the front end section which is rigid, up to the bent portion.

One end of the shape memory element is mechanically connected to the movable section of the optical mechanism which includes the movable section, and the other end of the shape memory element is fixed to a fixing section provided inside the bent portion.

Relative positions of the movable sections of the optical mechanism which includes the movable section, and the fixing section provided inside the bent portion, are changed by expansion and contraction of the shape memory element.

DETAILED DESCRIPTION OF THE INVENTION

Embodiments of an endoscope apparatus according to the present invention will be described below in detail by referring to the accompanying diagrams. However, the present invention is not restricted to the embodiments which will be described below.

First Embodiment

Figure 1:
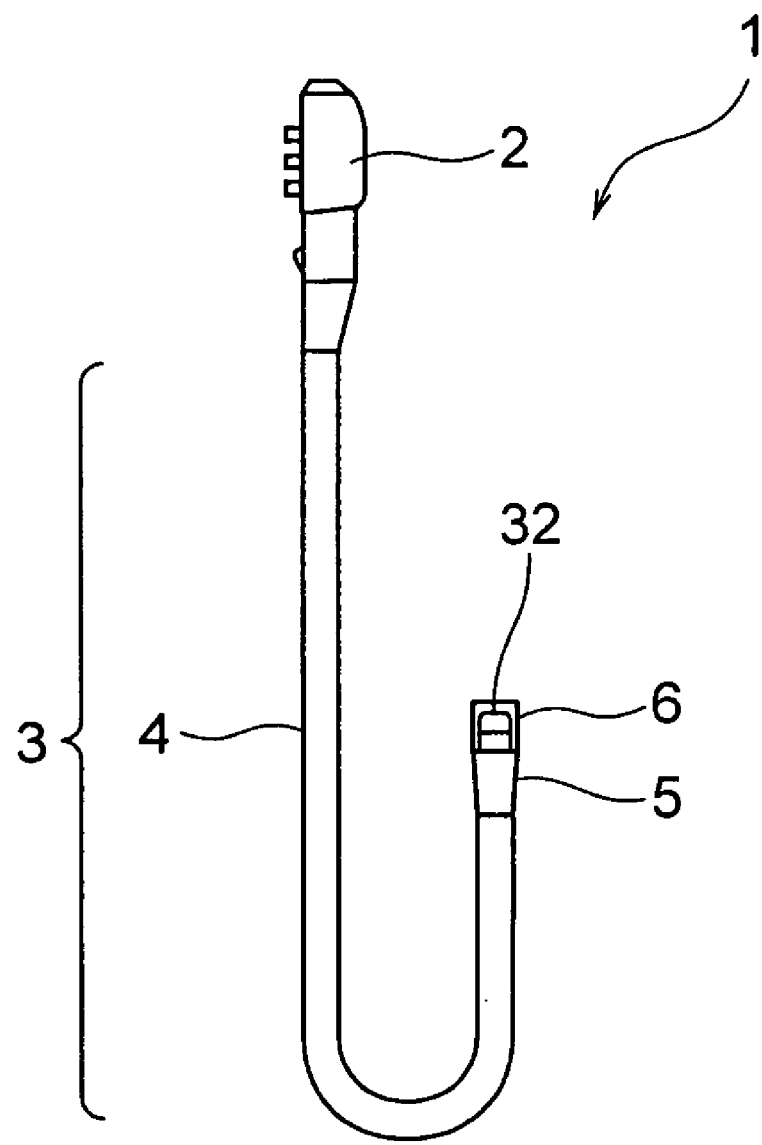
FIG. 1 is a diagram showing a schematic view of an entire endoscope apparatus according to a first embodiment of the present invention.

FIG. 1 shows a schematic view of an endoscope apparatus according to a first embodiment of the present invention. As shown in FIG. 1, an endoscope 1 includes an operating section 2 which performs a bending operation and a control of a pipe conduit system, and an inserting section 3 of which a rear end side is connected to the operating section 2, and which is inserted into a body cavity of a body to be examined.

The inserting section 3 includes a flexible tube 4, a bending section 5 which can be bent, and which is provided at a front end side of the flexible tube 4, and a front end section 6 which is rigid, and which is provided at a front end side of the bending section 5. The front end section 6 includes an imaging unit 32 which is built in, and which takes an image of a portion inside a body cavity which is being observed. The imaging unit 32 will be described later.

Figure 2:
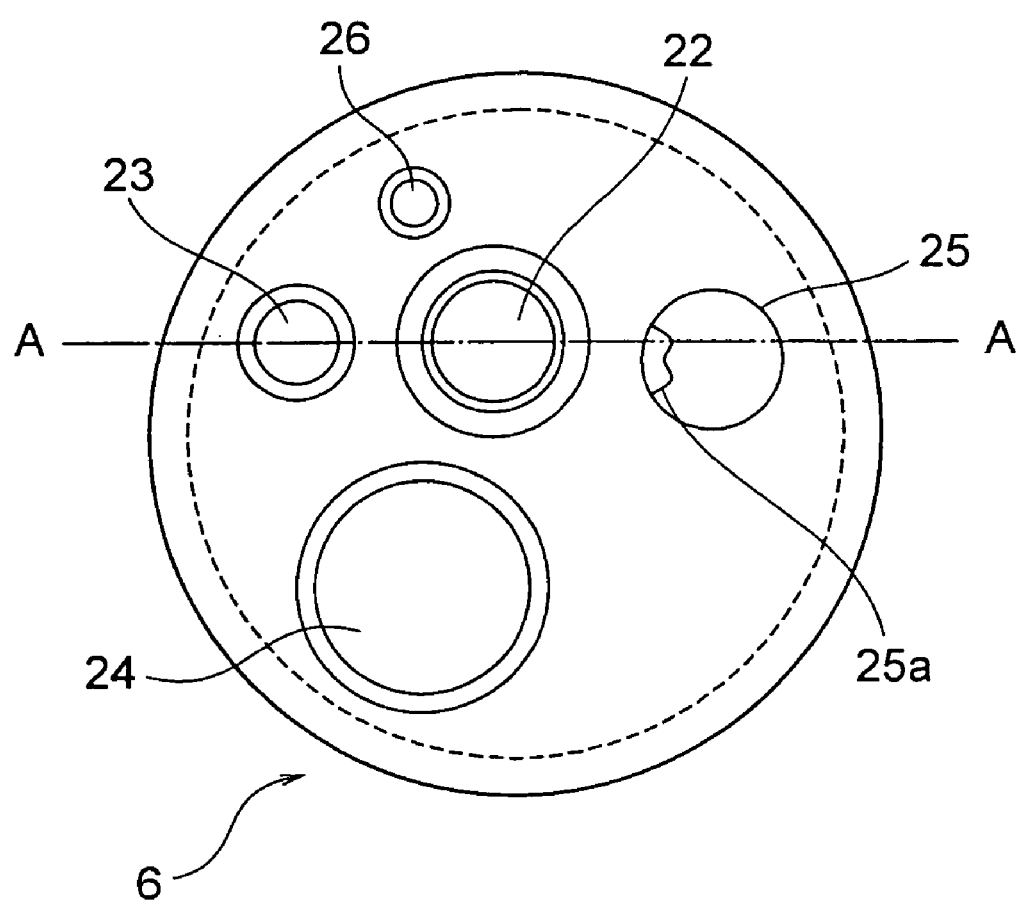
FIG. 2 is a diagram showing a front view of the endoscope apparatus according to the first embodiment.

FIG. 2 shows a front view of an inserting front end section of the endoscope 1 shown in FIG. 1. As shown in FIG. 2, a front end surface 21 of the front end section 6 includes an observation window 22 as a lens, which includes the imaging unit 32, an illumination window 23 as a lens which includes light guiding units, a channel aperture section 24 for inserting an endoscopic instrument, a gas and water nozzle 25 which is an aperture section of a gas and water channel 25a for cleaning the observation window 22, and a channel aperture section 26 which is an aperture section of forwarding water channel for cleaning body fluids such as blood and mucus of a diseased part of a person examined.

Figure 3:
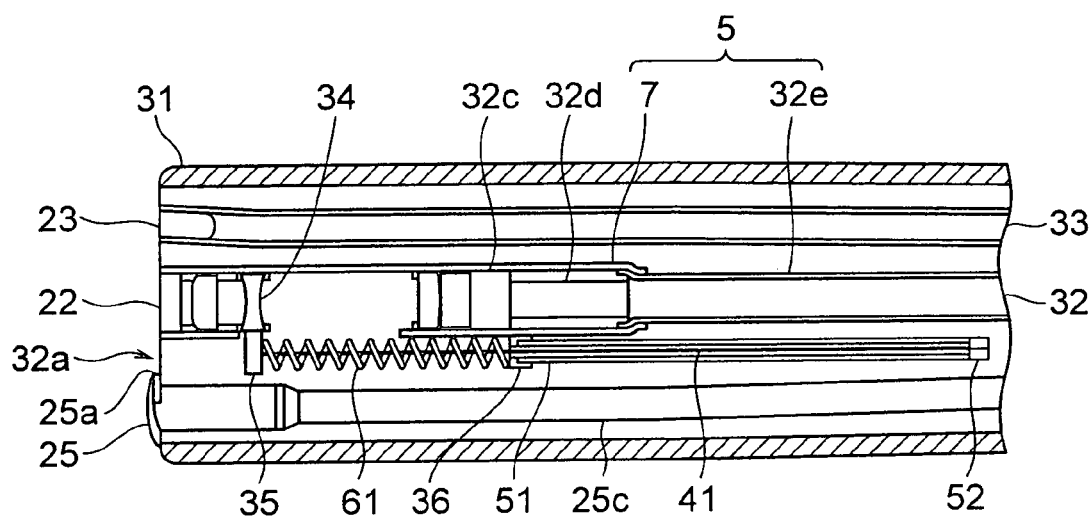
FIG. 3 is a diagram showing a cross-sectional view of the endoscope apparatus according to the first embodiment.
Figure 4:
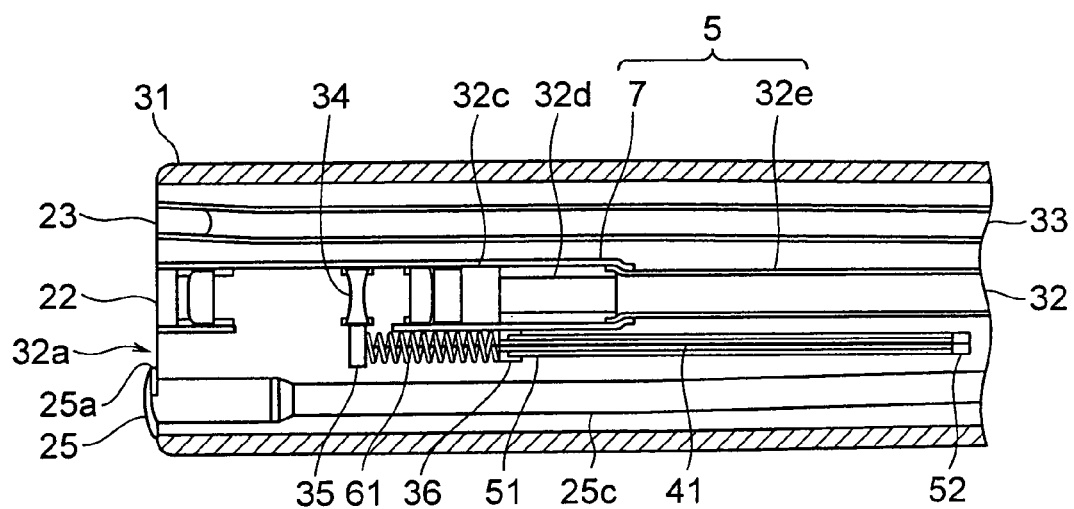
FIG. 4 is a diagram showing another cross-sectional view of the endoscope apparatus according to the first embodiment.

FIG. 3 and FIG. 4 show a cross-sectional view of a front end section to be inserted, along a line A-A in FIG. 2. As shown in FIG. 3, the front end section 6 is provided with a rigid front end section main body. Built-in components such as the imaging unit 32 corresponding to the observation window 22, and light guiding unit 33 corresponding to the illuminating window 23 are installed in the front end section main body. Moreover, the front end section main body is covered by a front end cover 31.

The imaging unit 32 includes the observation window 22, an objective optical system 32a which is provided at a rear end side of the observation window 22, and which is formed by a plurality of lens groups, an imaging device 32c which is a solid imaging device such as a CCD (Charge Coupled Device) provided at a rear end side of the objective optical system, and a circuit board 32d which is connected to the imaging device 32c, and which performs various processes such as signal amplification, and the imaging unit 32 is held by a lens barrel 7.

A signal wire 32e which is extended from the circuit board 32d is inserted in the imaging unit 32 through an inserting section 3. The objective optical system 32a includes a movable lens 34. Moreover, the movable lens 34 is supported by a movable lens frame 35. The movable lens frame 35 corresponds to a movable section. The objective optical system 32a and the movable lens frame 35 correspond to an optical mechanism.

Moreover, one end of a shape memory element 41 in the form of a wire is fixed to the movable lens frame 35. The shape memory element 41 is accommodated in a tube 51 which can be bent, which is fixed to a tube fixing member 36 of the lens barrel 7.

One end of a bias-applying coil spring 61 is also fixed to the tube fixing member 36. The other end of the bias-applying coil spring 61 is fixed to the movable lens frame 35. Moreover, the movable lens frame 35 is in a state of being pushed by a stress (bias or force imparted) by the bias-applying coil spring 61. When the shape memory element 41 is in a state of not being deformed by the stress of the bias-applying coil spring 61, the movable lens 34 is in a state of being held at a constant position.

The tube 51 which accommodates the shape memory element 41 is inserted in to a bent section 5 which is formed to have a tapered shape becoming thicker progressively from an inner side of the front end section 6 to a side of the front end section 6. In the flexible tube 4, one end of the tube 51 is clamped to each one end of the shape memory element 41, by a caulking for fixing 52. Accordingly, one end of the shape memory element 41 is fixed. The shape memory element 41 has a peculiarity of contracting when heated up to a transformation temperature, and slackening when cooled down up to the transformation temperature. Thus, a shape memory alloy in the form of a wire which expands and contracts according to the temperature is used as the shape memory element 41.

FIG. 3 shows a state of the movable lens 34 being driven by deforming the shape memory element 41 from a state shown in FIG. 3. An energizing unit (not shown in the diagram) applies a voltage to both ends of the shape memory element 41, and heats up the shape memory element 41 beyond the transformation temperature. Accordingly, the shape memory element 41 is contracted.

A force which generates contraction of the shape memory element 41 is greater than the stress applied by the bias-applying coil spring 61. Therefore, when a length of the shape memory element 41 becomes shorter than a distance between the one end fixed to one end of the tube 51 and a connecting point with the movable lens frame 35, the movable lens 34 moves.

In the first embodiment, both the tube 51 and the shape memory element 41 can be bent, and are structured such that even when in the bent state, there is no effect on a drive of the movable lens 34 which is a driving section. Moreover, the shape memory element 41 can be inserted into the bent section 5 of the endoscope, and can be extended up to the flexible tube 4 of the endoscope. Therefore, it is possible to secure a substantial length of the shape memory element 41.

Moreover, by using the shape memory element 41 having a small diameter, it is possible to reduce a diameter of the flexible tube 4. Furthermore, as mentioned earlier, it is possible to secure the substantial length of the shape memory element 41. Therefore, it is possible to increase an amount of change in the length by a phase transition of the shape memory element 41. As a result of this, it is possible to increase a change in relative positions of the movable lens 34 and one end of the tube 51. Consequently, it is possible to provide an endoscope apparatus which is capable of increase an amount of a change in position of the movable section of the optical mechanism for focusing, such as the movable lens 34. Moreover, since the structure inside the front end section 6 of the endoscope is a simple mechanical connection between the shape memory element 41 and the movable section of the optical mechanism, it is possible to reduce a radial direction of the front end section 6.

Moreover, in the first embodiment, in a case of moving the movable lens 34 by the change in the length of the shape memory element 41, by the phase transition of the shape memory element 41, by causing to make a transition to an original phase after the phase transition, the movable lens 34 is returned to the original position. Since the phase transition occurs due to a temperature change, as a character of the shape memory element 41, a traveling speed of the movable lens 34 is determined with a speed of the temperature change.

By using the bias-applying coil spring 61, a force acting in a direction opposite to a direction in which the movable lens 34 is moved due to the phase transition of the shape memory element 41, is exerted on the movable lens 34. Accordingly, it is possible to increase the speed at the time of transition of the shape memory element 41 to the original phase. Therefore, a driving speed of the movable lens 34 is increased.

Moreover, a relative distance between a front end of the shape memory element 41 and a front end of the tube 51 changes according to a clearance between an inner diameter of the tube 51, and an outer diameter of the shape memory element 41. Therefore, it is desirable to perform designing upon estimating an amount of change according to the clearance. An amount of change in the relative distance depending on the clearance of diameters is not required to be taken into consideration when the structure is such that the front end of the shape memory element 41 is stopped by abutting against a stopper which will be described later.

Moreover, it is desirable to use a non-conductive (insulation) tube 51, when the shape memory element 41 is to be transformed by heating by energizing. Accordingly, when being energized (when the electric power is supplied), the shape memory element 41 does not have electrical influence from outside or from within the shape memory element 41. Therefore, it is possible to drive the shape memory element 41 efficiently. Moreover, as a matter of course, a method for heating the shape memory element 41 is not restricted to energizing by electric power, and may be any other method.

Second Embodiment

Figure 5:
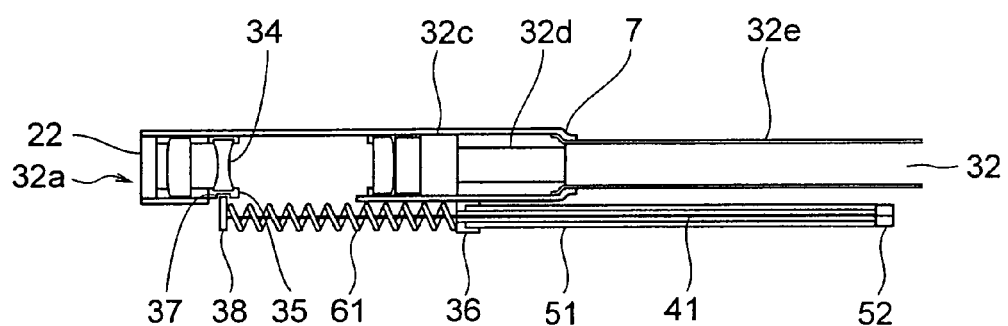
FIG. 5 is a diagram showing a cross-sectional view of an endoscope apparatus according to a second embodiment.

FIG. 5 shows a cross-sectional view of an endoscope apparatus according to a second embodiment of the present invention. Same reference numerals are assigned to components same as in the first embodiment, and a description to be repeated is omitted. FIG. 5 shows a vicinity of the imaging unit 32 in a cross-sectional view of a front end section along the line A-A in FIG. 2.

The movable lens frame 35 has a groove 37. The shape memory element 41 and the bias-applying coil spring 61 are fixed to a connecting member 38. Moreover, the connecting member 38 is fitted in the groove 37. The structure is such that there exists a minute gap between the connecting member 38 and the groove 37.

By the connecting member 38 maintaining the gap from the groove 37 of the movable lens frame 35, even when an axis in a driving direction of the movable lens frame 35 and an axis in a direction of change of shape of the shape memory element 41 are misaligned by a small amount, the gap absorbs the misalignment. Therefore, it is possible to prevent a decline in a driving speed, or stopping of driving due to hitching of the movable lens frame 35.

In other words, due to the gap, even when an axis in a direction of movement of the movable lens 34 which is determined by the lens barrel 7, and an axis in a direction of deformation by heating of the shape memory element 41 do not coincide perfectly, it is possible to perform the drive smoothly. Moreover, although it is not shown in the diagram, the groove 37 may be formed around the entire outer circumference of the movable lens frame 35. In this case, even when the connecting member 38 is shifted in a direction vertical to the driving direction of the movable lens 34, it is possible to perform the drive smoothly and efficiently.

Third Embodiment

Figure 6:
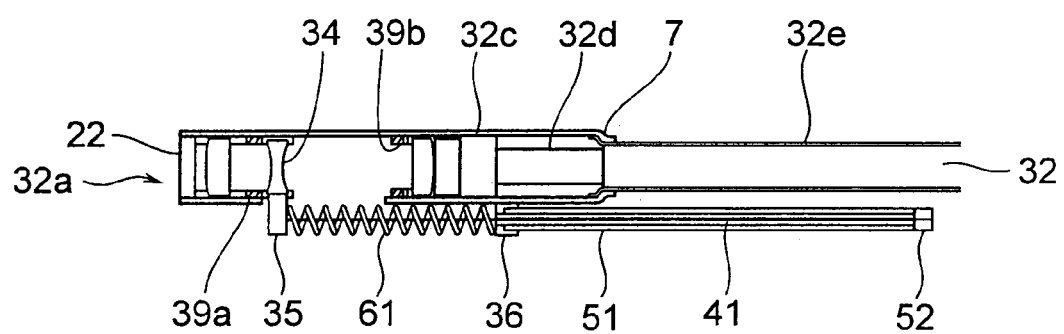
FIG. 6 is a diagram showing a cross-sectional view of an endoscope apparatus according to a third embodiment.
Figure 7:
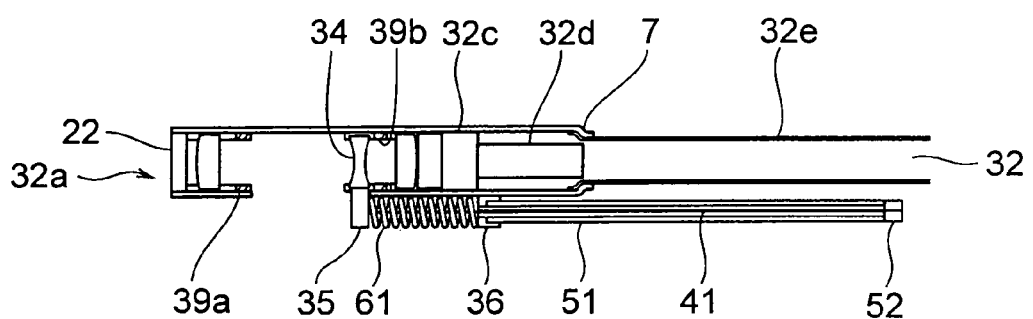
FIG. 7 is another diagram showing the cross-sectional view of the endoscope apparatus according to the third embodiment.

FIG. 6 and FIG. 7 show cross-sectional views of an endoscope apparatus according to a third embodiment of the present invention. Same reference numerals are assigned to components same as in the first embodiment, and a description to be repeated is omitted. FIG. 6 and FIG. 7 show a vicinity of the imaging unit 32 in a cross-sectional view of the front end section along the line A-A in FIG. 2.

In the third embodiment, stoppers 39a and 39b are installed on a movable area (range of movement) of the movable lens 34 in the lens barrel 7. The stoppers 39a and 39b are installed at positions abutting against the movable lens frame 35 in two states namely a state in which the shape memory element 41 is slackened, and a state in which the shape memory element 41 is contracted up on being heated up.

FIG. 6 shows a state in which the movable lens frame 35 is stopped upon being abutted against the stopper 39a shown on a left side in FIG. 6, due to the stress exerted by the bias-applying coil spring 61, as the shape memory element 41 is in the slackened state.

Whereas, FIG. 7 shows a state in which the movable lens frame 35 connected to the shape memory element 41, is pulled as the shape memory element 41 is contracted due to the phase transition upon being heated up due to the voltage applied by an energizing unit (not shown in the diagram) on both ends of the shape memory element 41. The movable lens frame 35 is stopped upon being abutted against the stopper 39b shown on a right side in FIG. 7. Due to the stoppers 39a and 39b, the movable lens 34 can be stopped accurately at least at two positions. Positions at which the stoppers 39a and 39b are to be provided are not restricted to be inside the lens barrel 7.

In the third embodiment, due to the stoppers 39a and 39b, a driving area (driving range) of the movable lens frame 35 is limited, and it is possible to perform accurately a position control at least at two points, by a simple mechanism. Moreover, when the bias-applying coil ring 61 is there, when the movable lens frame 35 is not being driven by a change in the shape of the shape memory element 41, it is possible to hold by the stopper 39a. As a result of this, it is possible to perform an accurate position control by a simple structure.

Fourth Embodiment

Figure 8:
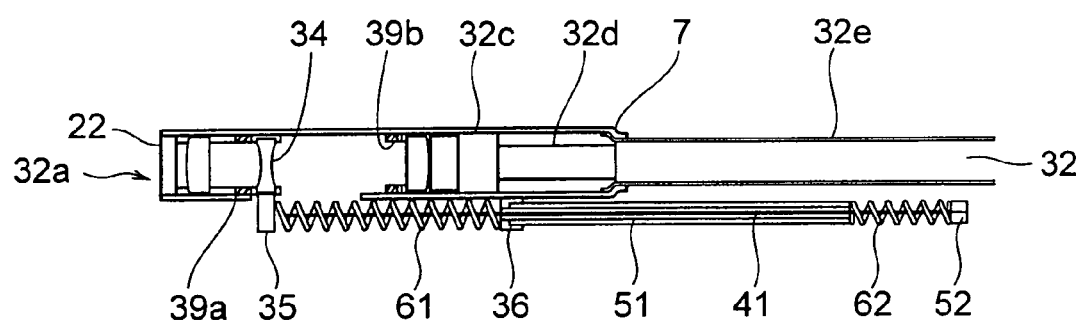
FIG. 8 is a diagram showing a cross-sectional view of an endoscope apparatus according to a fourth embodiment of the present invention.
Figure 9:
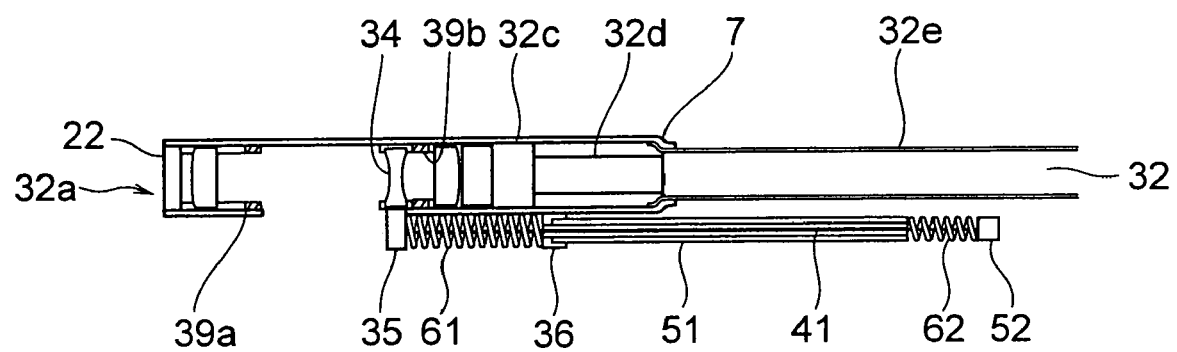
FIG. 9 is another diagram showing the cross-sectional view of the endoscope apparatus according to the fourth embodiment.

FIG. 8 and FIG. 9 show cross-sectional views of an endoscope apparatus according to a fourth embodiment of the present invention. Same reference numerals are assigned to components same as in the first embodiment, and a description to be repeated is omitted. FIG. 8 and FIG. 9 show a vicinity of the imaging unit 32 in a cross-sectional view of the front end section along the line A-A in FIG. 2.

FIG. 8 shows a structure in which a buffering coil spring 62 is installed between the one end of the tube 51 and the caulking for fixing 52. The buffering coil spring 62 is installed such that the buffering coil spring 62 is fixed at the one end of the tube 51 and at one end of the caulking for fixing 52. Moreover, one end of the shape memory element 41 is fixed by the caulking for fixing 52.

FIG. 8 shows a state in which the shape memory element 41 is slackened, and the movable lens frame 35 is pushed upon exerting the stress (bias or force imparted) by the bias-applying coil spring 61 and the buffering coil spring 62. FIG. 9 shows a state in which the movable lens frame 35 is pulled upon contraction of the shape memory element 41 by the phase transition upon being heated. In this state, the movable lens frame 35 is abutted against the stopper 39b. The movable lens frame 35 cannot move further in a right direction in FIG. 9 beyond the position of the stopper 39b. Therefore, when the shape memory element 41 is heated to a temperature at which the shape memory element 41 can be contracted further, due to an overload on the shape memory element 41, a life of the shape memory element 41 is shortened, or the shape memory element 41 is damaged.

In the fourth embodiment, for preventing the overload from being exerted on the shape memory element 41, the structure is such that an amount of displacement equal to a length of the contraction of the shape memory element 41 is absorbed by the contraction of the buffering coil spring 62.

When a spring constant of the buffering coil spring 62 is greater than a spring constant of the bias-applying coil spring 61, when the movable lens 34 is driven, only the bias-applying coil spring 61 is contracted. Therefore, the contraction of the shape memory element 41 is transmitted efficiently to the movable lens 34. As a result of this, the driving efficiency is improved.

From a point of view of a structure of the movable lens frame 35 of the optical mechanism, for example in the state in which the drive is stopped forcibly by the abutting of the movable lens frame 35, when the shape memory element 41 is supported by a length shorter than the change in length of the phase transition of the shape memory element 41 due to the heating, the overload is exerted on the shape memory element 41. As a result of this, the life of the shape memory element 41 is shortened. In the fourth embodiment, it is possible to prevent the exerting of the overload on the shape memory element 41 by absorbing the change in length of the amount of the change in length of the phase transition, by the buffering coil spring 62. Furthermore, it is possible to convert a substantial portion of the change in length of the shape memory element 41 to a displacement of the movable lens frame 35.

Fifth Embodiment

Figure 10:
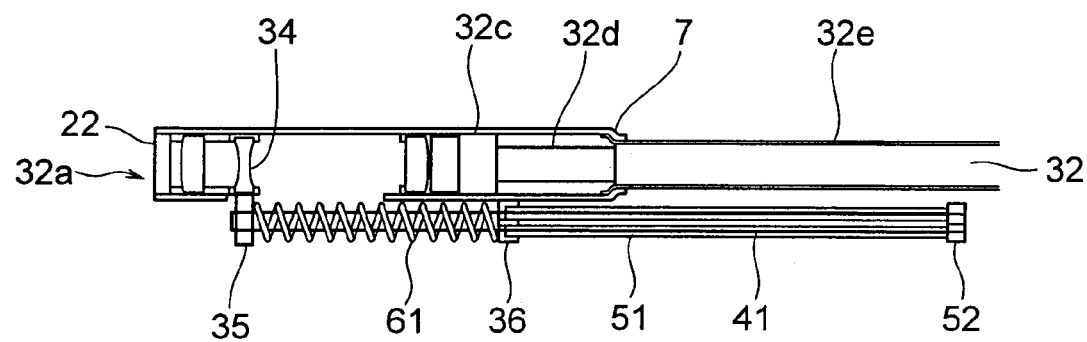
FIG. 10 is a diagram showing a cross-sectional view of an endoscope apparatus according to a fifth embodiment.

FIG. 10 shows a cross-sectional view of an endoscope apparatus according to a fifth embodiment of the present invention. Same reference numerals are assigned to components same as in the first embodiment, and a description to be repeated is omitted. FIG. 10 shows a vicinity of the imaging unit 32 in a cross-sectional view of the front end section along the line A-A in FIG. 2.

In the fifth embodiment, the shape memory element 41 is connected to the movable lens frame 35 in a state bent in a U-shape form. Each of the shape memory elements 41 which have become two in number upon bending, is accommodated in the tube 51. The tube 51 is fixed to the lens barrel 7 by the tube fixing member 36. The both ends of the shape memory element 41 are fixed to one end of the 51 by being clamped by the caulking for fixing 52.

The shape memory element 41 is heated by applying the voltage by the energizing unit (not shown in the diagram), and the movable lens 34 is driven. At this time, the both ends of the shape memory element 41 can be disposed at one place. Therefore, an energizing mechanism can be simplified. Moreover, regarding the shape memory element 41, a surface area of the two shape memory elements 41 upon bending is greater as compared to one shape memory element 41 having a cross-sectional area of a diameter same as a total cross-sectional area of two diameters. Therefore, it is possible to drive efficiently by raising up a heat radiation effect with respect to the change in temperature occurred due to the driving. Furthermore, since it is possible to make the diameter of the shape memory element 41 smaller, the endoscope apparatus can be assembled easily.

Furthermore, in a case of driving the movable lens frame 35 by the change in the shape by energizing and heating the shape memory element 41, by connecting upon bending the shape memory element 41, the number of shape memory elements 41 related to the drive becomes two. Therefore, a driving force is increased.

Sixth Embodiment

Figure 11:
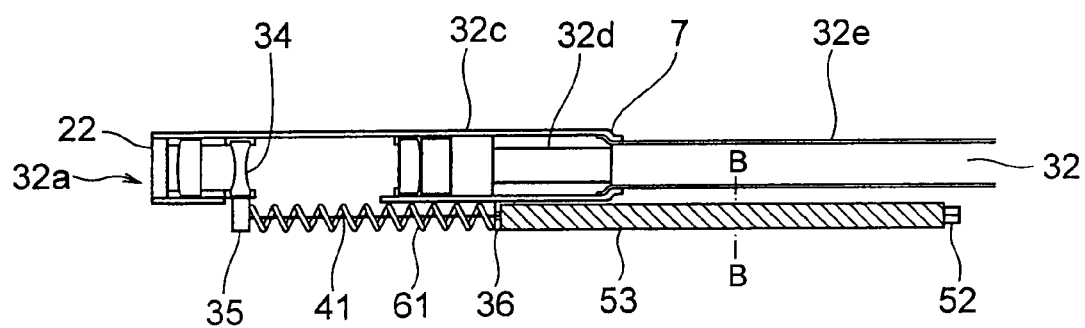
FIG. 11 is a diagram showing a cross-sectional view of an endoscope apparatus according to a sixth embodiment.
Figure 12:
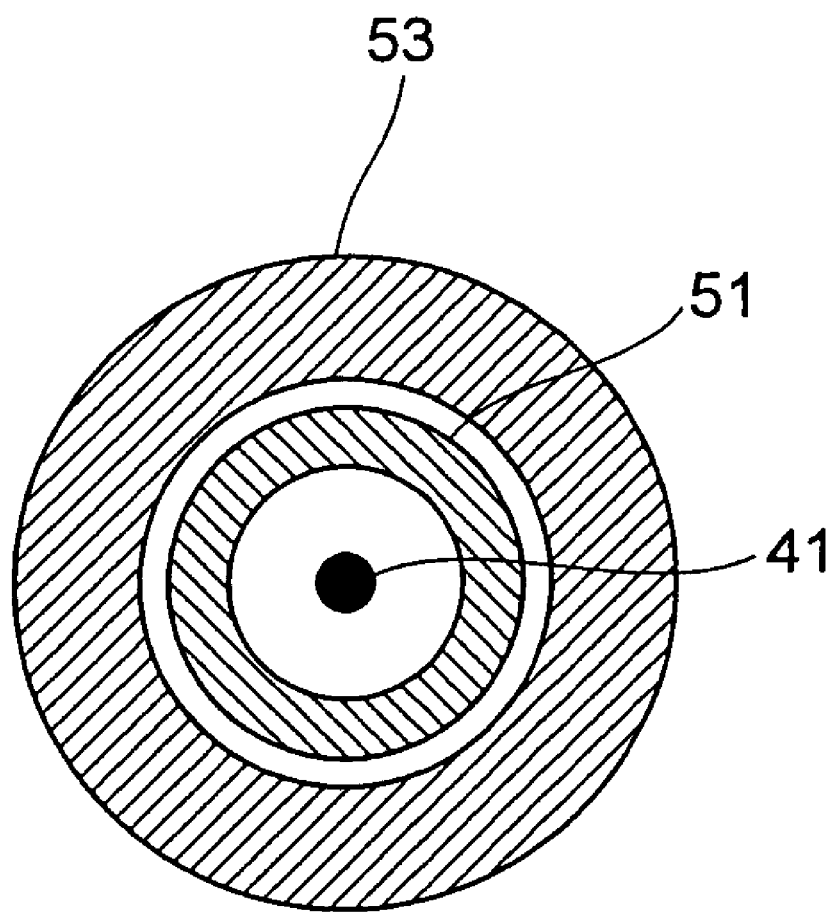
FIG. 12 is another diagram showing the cross-sectional view of the endoscope apparatus according to the sixth embodiment.

FIG. 11 and FIG. 12 show cross-sectional views of endoscope apparatus according to a sixth embodiment of the present invention. Same reference numerals are assigned to components same as in the first embodiment, and a description to be repeated is omitted. FIG. 11 shows the vicinity of the imaging unit 32 in the cross-sectional view of the front end section along the line A-A in FIG. 2. FIG. 12 shows a cross-sectional view along a line B-B in FIG. 11.

FIG. 11 shows a structure in which the tube 51 is accommodated in a contact spring 53 having a coefficient of elasticity higher than a coefficient of elasticity of the tube 51. One end of the contact spring 53 is fixed to the lens barrel 7 by the tube fixing member 36 together with the tube 51. The other end of the contact spring 53 is clamped at the caulking for fixing 52, and is fixed to one end of the shape memory element 41 and the tube 51.

When there is a strong occurrence of the change in the length due to the phase transition of the shape memory element 41, the tube 51 is deformed. Moreover, a length of the tube 51 is changed. Therefore, for transmitting efficiently the occurrence of the change in the length of the shape memory element 41 to the movable lens 34, the length of the tube 51 should not change the occurrence of the change in length of the shape memory element 41.

Therefore, as in the sixth embodiment, the structure is made such that the tube 51 is covered by the control spring 53 having the high coefficient of elasticity. Accordingly, when the occurrence of the shape memory element 41 is strong, it is possible to prevent the deformation of the tube 51. Moreover, it is possible to maintain a distance between one end of the tube 51 which fixes the shape memory element 41, and a connecting portion of the shape memory element 41 and the movable lens frame 35. Therefore, it is possible to drive the movable section efficiently.

Moreover, the contact spring 53 can be bent freely, and a change in a length in a longitudinal direction of the contact spring is small. Therefore, it is possible to maintain a distance between one end of the tube 51 fixing the shape memory element 41 and the connecting portion of the shape memory element 41 and the movable lens frame 35, which is an important factor in driving the movable lens 34. In other words, it is possible to improve durability.

Moreover, the contact spring 53 can have a similar effect even as a cable which includes a wire. FIG. 12 shows a cross-sectional view of the shape memory element 41 covered by the tube 51 and the contact spring 53. When the contact spring 53 is metallic, a thermal conductivity of the contract spring 53 is higher than a thermal conductivity of the tube 51. Therefore, a heat radiation effect works. As a result of this, at the time of slackening the shape memory element 41 by decreasing the temperature of the shape memory element 41 which is contracted by heating due to the driving of the movable lens 34, a speed of cooling (speed of decreasing temperature) of the shape memory element 41 is increased. As a result of this, since a speed of the phase transition due to the cooling is increased, the driving speed of the movable lens 34 in a direction opposite to a direction when the shape memory element 41 was heated is increased.

Seventh Embodiment

Figure 13:
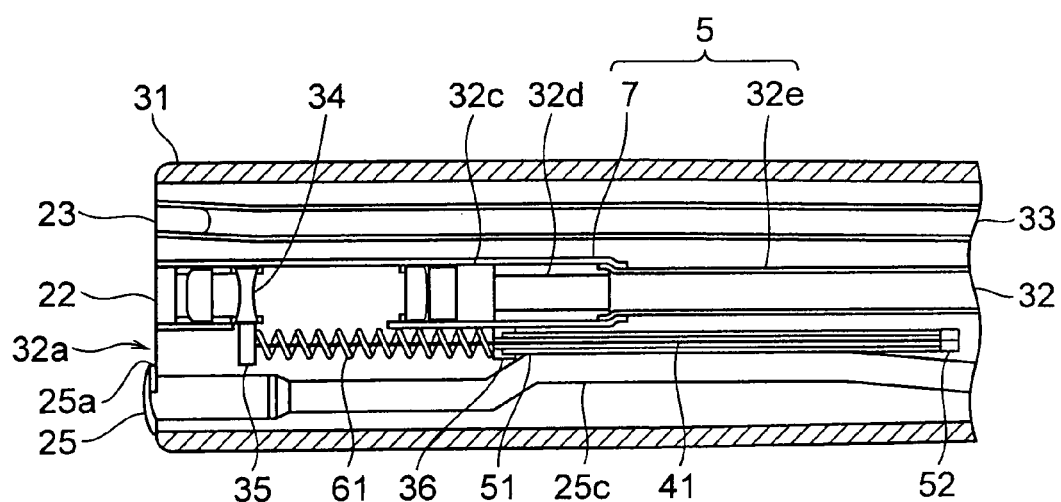
FIG. 13 is a diagram showing a cross-sectional view of an endoscope apparatus according to a seventh embodiment.

FIG. 13 is shows a cross-sectional view of an endoscope apparatus according to a seventh embodiment of the present invention. Same reference numerals are assigned to components same as in the first embodiment, and a description to be repeated is omitted. FIG. 13 shows a cross-sectional view of the front end section along the line A-A in FIG. 2.

FIG. 13 shows a view in which the gas-water supply tube 25c comes in a contact partially with the tube 51. Heat which exists inside the tube 51 is transmitted to the gas-water supply tube 25c in contact. Consequently, a heat of the shape memory element 41 heated at the time of driving the movable lens 34 is transmitted to the gas-water supply tube 25c via the tube 51.

The gas-water supply tube 25c being structured to allow a flow of liquid and gas, has a substantial heat radiation effect. In other words, the heat of the shape memory element 41 which is heated is radiated or cooled down by the gas-water supply tube 25c, via the tube 51. Therefore, at the time of slackening the shape memory element 41 by decreasing the temperature of the shape memory element 41 which is contracted by heating due to the driving of the movable lens 34, a speed of decreasing the temperature is increased. As a result of this, the driving speed of the movable lens 34 in a direction opposite to the direction when the shape memory element 41 was heated is increased.

The gas-water supply tube 25c corresponds to a gas pipe conduit and a water pipe conduit. Moreover, the tube 51 is not restricted to make a contact with the gas-water supply tube 25c, and may make a contact with a pipe conduit such as a forceps channel.

Eighth Embodiment

Figure 14:
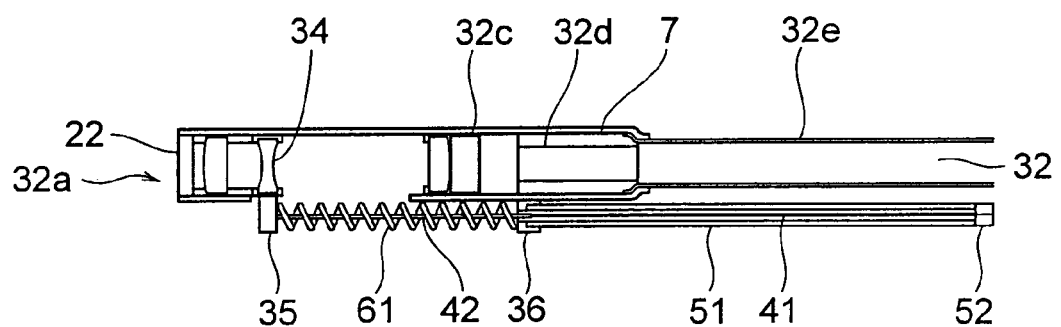
FIG. 14 is a diagram showing a cross-sectional view of an endoscope apparatus according to an eighth embodiment.

FIG. 14 shows a cross-sectional view of an endoscope apparatus according to an eighth embodiment. Same reference numerals are assigned to components same as in the first embodiment, and a description to be repeated is omitted. FIG. 14 shows the vicinity of the imaging unit 32 in a cross-sectional view of the front end section along the line A-A in FIG. 2.

A connecting wire 42 is connected to the movable lens frame 35. The connecting wire 42, when viewed from a radial direction of the front end section 6, is connected to the shape memory element 41, at a position toward the flexible tube 4, farther than the imaging device 32c. Consequently, the shape memory element 41 is disposed at a position away from the imaging device 32c. The shape of the shape memory element 41 is changed near the transformation temperature, and the shape memory element 41 is contracted.

By disposing the shape memory element 41 sufficiently away from the image device 32c, it is possible to prevent the shape memory element 41 from being heated due to the radiation of heat from the imaging device 32c, and to prevent the change in the shape due to the change in the length by the phase transition of the shape memory element 41. As a result of this, it is possible to prevent a malfunction of the movable lens 34 due to the radiation of heat from the imaging device 32c.

Ninth Embodiment

Figure 15:
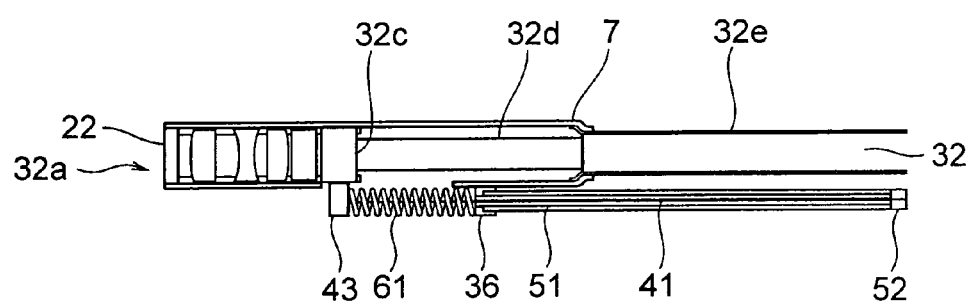
FIG. 15 is a diagram showing a cross-sectional view of an endoscope apparatus according to a ninth embodiment.

FIG. 15 shows a cross-sectional view of an endoscope apparatus according to a ninth embodiment of the present invention. Same reference numerals are assigned to components same as in the first embodiment, and a description to be repeated is omitted. FIG. 15 shows the vicinity of the imaging unit 32 in the cross-sectional view of the front end section along the line A-A in FIG. 2.

The imaging device 32c is supported by a movable imaging device frame 43. Moreover, the shape memory element 41 is connected to the movable imaging device frame 43. Two ends of the bias-applying coil spring 61 are fixed to the movable imaging device frame 43 and the tube fixing member 36 respectively. Moreover, the tube fixing member 36 is fixed to the lens barrel 7. Therefore, by the stress of the bias-applying coil spring 61, the movable imaging device frame 43 is in a pushed state.

The shape memory element 41 is allowed to contract by heating up to the temperature higher than the temperature at which the phase transition occurs, by applying the voltage to both ends of the shape memory element 41 by the energizing unit (not shown in the diagram). Accordingly, the movable imaging device frame 43 is driven upon being pulled by a force generated by the contraction of the shape memory element 41. It is possible to perform focusing by changing relative positions of the imaging device 32c and the objective optical system 32a, by moving the movable imaging device frame 43.

In the ninth embodiment, the shape memory element 41 is connected to the imaging device frame 43 at a portion near from the imaging device 32c. Therefore, most of the area of the shape memory element 41 is disposed at a position away from the imaging device 32c. Consequently, it is possible to prevent a malfunction of the movable imaging device frame 43 due to the contraction of the shape memory element 41, which is caused due to the radiation of heat from the imaging device 32.

Thus, in the ninth embodiment, one end of the shape memory element 41 and the imaging device frame 43 are connected mechanically. Accordingly, it is possible to minimize a portion of the area of the shape memory element 41 which is affected thermally by the imaging device 32c mechanically. Therefore, it is possible to prevent the thermal effect from the imaging device 32c.

Tenth Embodiment

Figure 16:
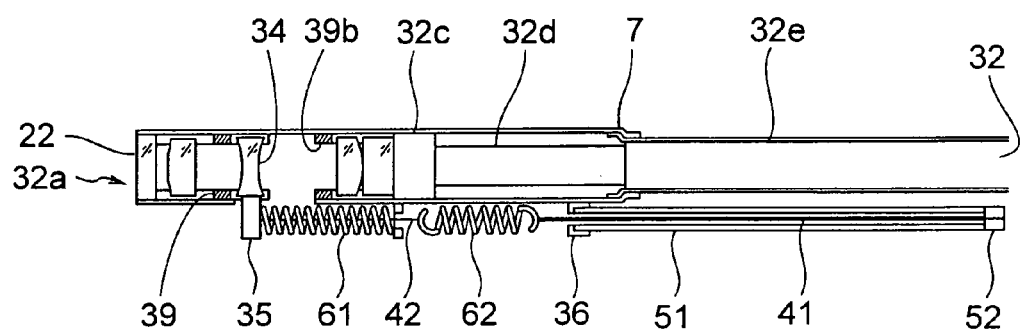
FIG. 16 is a diagram showing a cross-sectional view of an endoscope apparatus according to a tenth embodiment.
Figure 17:
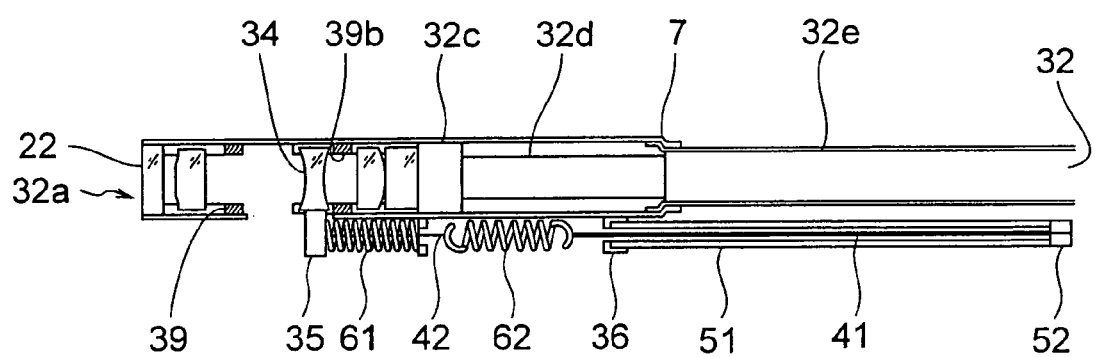
FIG. 17 is another diagram showing the cross-sectional view of the endoscope apparatus according to the tenth embodiment.
Figure 18:
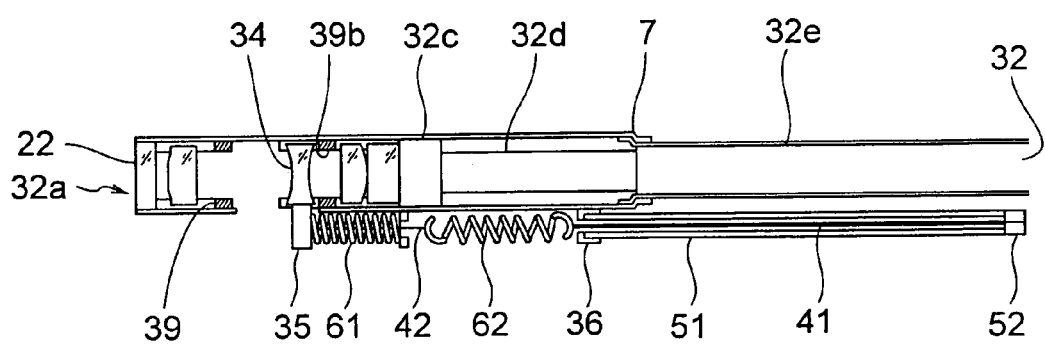
FIG. 18 is a still another diagram showing the cross-sectional view of the endoscope apparatus according to the tenth embodiment.

FIG. 16, FIG. 17, and FIG. 18 show cross-sectional views of an endoscope apparatus according to a tenth embodiment of the present invention. Same reference numerals are assigned to components same as in the first embodiment, and a description to be repeated is omitted. FIG. 16, FIG. 17, and FIG. 18 show the vicinity of the imaging unit 32 in the cross-sectional view of the front end section along the line A-A in FIG. 2.

In FIG. 16, one end of the connecting wire 42 is connected to the movable lens frame 35, and the other end of the connecting wire 42 is connected to one end of the buffering coil spring 62. The other end of the buffering coil spring 62 is connected to the shape memory element 41. The connecting wire 42 may be a shape memory element.

Furthermore, when the connecting wire 42, the bias-applying coil spring 61, and the shape memory element 41 are electrically connected, it is possible to cause the phase transition by heating both the connecting wire 42 and the shape memory element 41 by energizing.

FIG. 16 shows a state of the movable lens frame 35 pushed by the action of the stress (bias or force imparted) of the bias applying coil spring 61 due to slackening of the shape memory element 41. FIG. 17 shows a state of the movable lens frame 35 pulled by contraction due to the phase transition upon heating of the shape memory element 41. In this state, the movable lens frame 35 is abutted against the stopper 39b.

FIG. 18 shows a state in which the shape memory element 41 is contracted further than in the state in FIG. 17, and an amount of contraction of the shape memory element 41 is absorbed by drawing of the buffering coil spring 62. In FIG. 17, the movable lens frame 35 cannot cross the position of the stopper 39b and move further in right direction in FIG. 17.

Therefore, when the shape memory element 41 is heated up to a temperature at which the shape memory element 41 can be contracted, there is an overload on the shape memory element 41, and a performance of the shape memory element 41 is declined due to a lattice defect which occurs inside. In the tenth embodiment, for preventing such overload from being exerted on the shape memory element 41, the structure is such that the amount of displacement equal to the length of contraction of the shape memory element 41 is absorbed by the elongation of the buffering coil spring 62.

Furthermore, the buffering coil spring 62 absorbs an excessive contraction of the shape memory element 41 at a side of the movable lens frame 35 than at a side of the tube fixing member 36. Therefore, an entire length from the tube fixing member 36 up to the caulking for fixing 52 via the non-conductive tube 51 is maintained.

Consequently, in the flexible tube 4 of the endoscope, it is possible to prevent damage and destruction of other tubes and wires, which may be caused due to the change in the length from the tube fixing member 36 up to the caulking for fixing 52 via the tube 51 which is non-conductive.

Moreover, when the shape memory element 41 is heated by energizing, and a wire for energizing is connected to the caulking for fixing 52, it is possible to prevent a dame and breaking of a wire connecting portion for energizing, and a destruction of the wire for energizing which may be caused due to the change in the length from the tube fixing member up to the caulking for fixing 52 via the non-conductive tube 51.

By disposing the buffering coil spring 62 inside the rigid front end section 6 of the endoscope, an axis of the buffering coil spring 62 is maintained to be rectilinear, and the buffering coil spring 62 can function all the time, while maintaining characteristics in an unbent state.

Eleventh Embodiment

Figure 19:
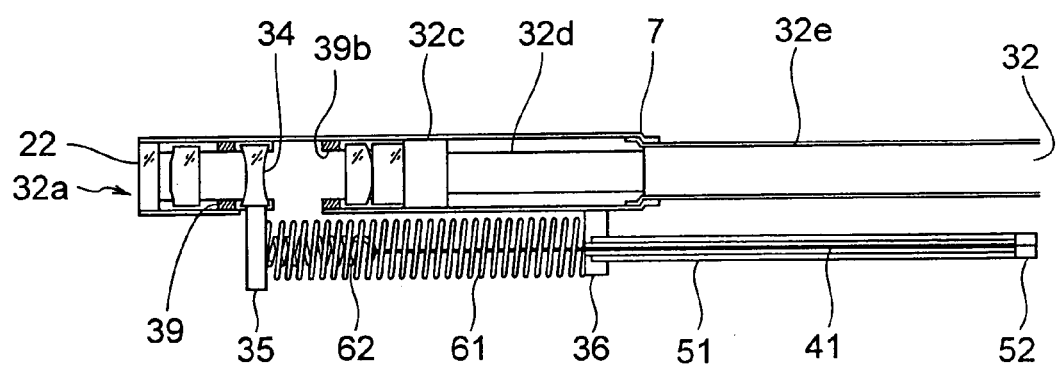
FIG. 19 is a diagram showing a cross-sectional view of an endoscope apparatus according to an eleventh embodiment.

FIG. 19 shows a cross-sectional view of an endoscope apparatus according to an eleventh embodiment. Same reference numerals are assigned to components same as in the first embodiment, and a description to be repeated is omitted.

As shown in FIG. 19, one end of the buffering coil spring 62 is fixed to the movable lens frame 35, and the other end of the buffering coil spring 62 is connected to one end of the shape memory element 41. An inner diameter of the bias-applying coil spring 61 is let to be greater than an outer diameter of the buffering coil spring 62, and the bias-applying coil spring 61 is disposed so as to accommodate the buffering coil spring 62.

In this arrangement, a length of the buffering coil spring 62 is accommodated in a length of the bias-applying coil spring 61, and it is possible to reduce a structural length of in an axial direction of the bias-applying coil spring 61 and the buffering coil spring 62 put together. Moreover, when the buffering coil spring 62 is disposed inside the rigid front end section 6 of the endoscope, it is possible to decrease a length of in an axial direction of the front end section 6 in the endoscope structure.

Twelfth Embodiment

Figure 20:
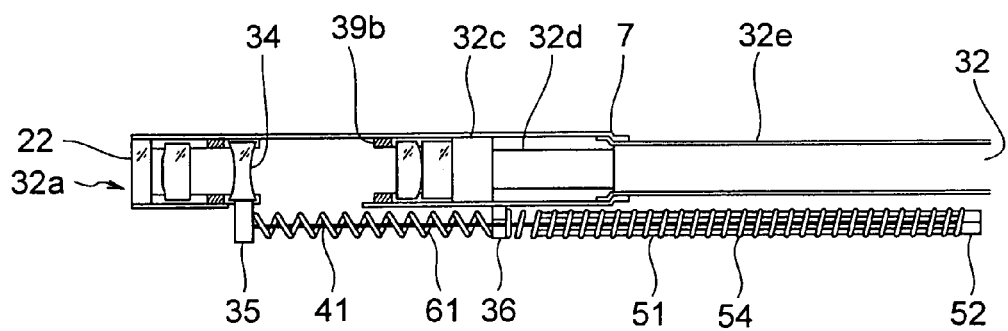
FIG. 20 is a diagram showing a cross-sectional view of an endoscope apparatus according to a twelfth embodiment.

FIG. 20 shows a cross-sectional view of an endoscope apparatus according to a twelfth embodiment of the present invention. Same reference numerals are assigned to components same as in embodiments from the first embodiment to the fourth embodiment, and the sixth embodiment, and a description to be repeated is omitted. FIG. 20 shows a vicinity of the imaging unit 32 in a cross-sectional view of the front end section along the line A-A in FIG. 2.

FIG. 20 shows a structure in which the tube 51 is accommodated in a protecting spring 54 which has a spring constant greater than the spring constant of the bias-applying coil spring 61. One end of the protecting spring 54 is fixed to the lens barrel 7, by the tube fixing member 36. The other end of the protecting spring 54 is clamped by the caulking for fixing 52, and fixes one end of the shape memory element 41 and the tube 51.

The movable lens frame 35 is pulled due to the change in the length of the shape memory element 41 by the phase transition of the shape memory element 41, and is abutted against the stopper 39b. In the state of abutted against the stopper 39b, the movable lens frame 35 cannot move further in a right direction in FIG. 20 beyond the position of the stopper 39b. Therefore, when the shape memory element 41 is heated to a temperature at which the shape memory element 41 can be contracted further, due to the overload on the shape memory element 41, the life of the shape memory element 41 is shortened.

In the twelfth embodiment, for preventing the overload from being exerted on the shape memory element 41, the structure is such that the amount of displacement equal to the length of contraction of the shape memory element 41 is absorbed by the contraction of the protecting spring 54. Moreover, the tube 51 is structured to be shorter than the protecting spring 54 by an amount of contraction of the protecting spring 54.

When the shape memory element 41 is heated by energizing, by letting the tube 51 to be a non-conductive member, an efficiency of energizing (supplying the electric power) of the shape memory element 41 is improved, and further, the protecting spring 54 being metallic, a heat radiation effect is improved, and therefore it is possible to improve the cooling effect at the time when not being heated.

The movable lens frame 35 moves when the length of the shape memory element 41 has become shorter than a distance between an end at which the protecting spring 54 and the shape memory element 41 are fixed, and a portion at which the other end of the shape memory element 41 and the movable lens frame 35 are fixed, due to the change in the length by the phase transition.

The protecting spring 54 being serving both roles namely a role of determining a length which has an effect on the movement, and a role of absorbing the excessive amount of contraction of the shape memory element 41, the structure is simplified.

In the twelfth embodiment, the tube 51 is structured to have a length shorter than the length of the protecting spring 54, and when the tube 51 has a sufficient contractibility, letting the equal (same) length as the protecting spring 54, the same effect is achieved by fixing to the tube fixing member 36 together with the protecting spring 54.

Thirteenth Embodiment

Figure 21:
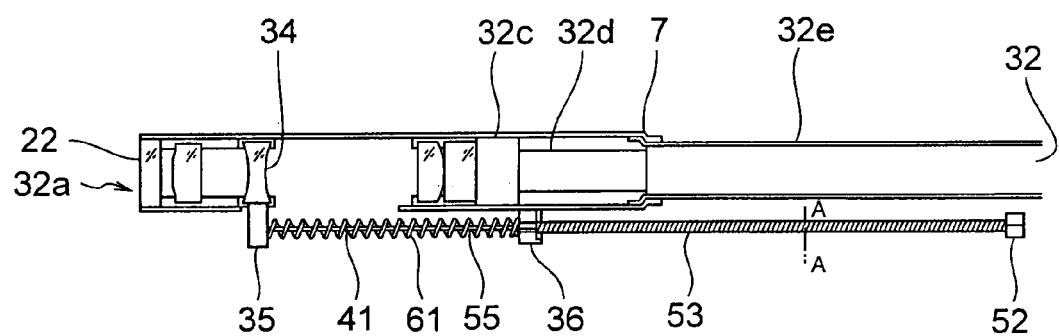
FIG. 21 is a diagram showing a cross-sectional view of an endoscope apparatus according to a thirteenth embodiment.
Figure 22:
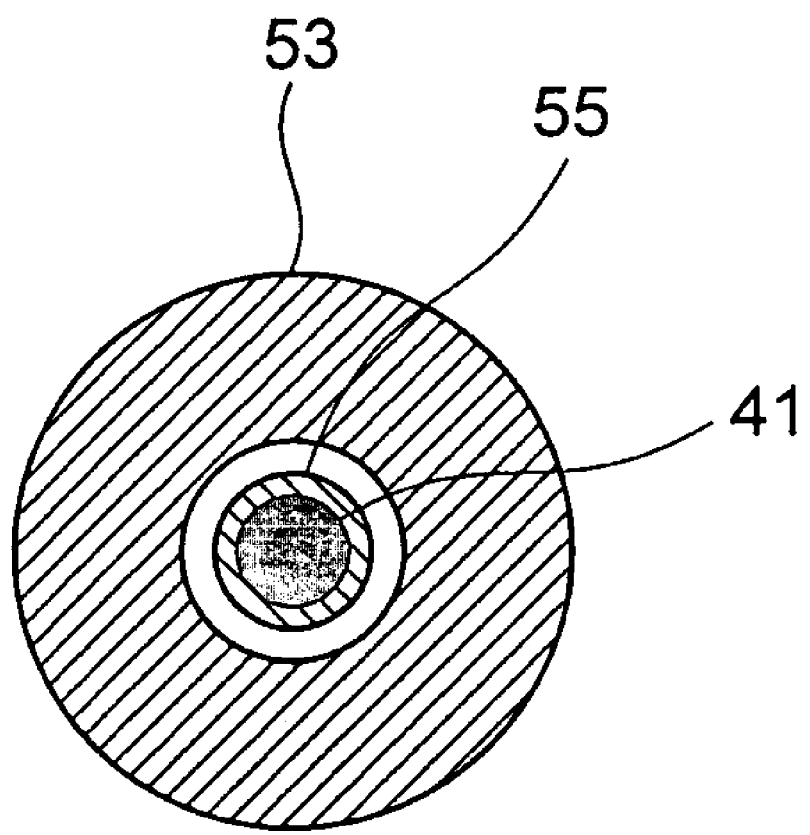
FIG. 22 is another diagram showing the cross-sectional view of the endoscope apparatus according to the thirteenth embodiment.

FIG. 21 shows a cross-sectional view of an endoscope apparatus according to a thirteenth embodiment of the present invention. Same reference numerals are assigned to components same as in the embodiments described above, and a description to be repeated is omitted. FIG. 22 shows a vicinity of the imaging unit 32 in a cross-sectional view of a front end section along a line A-A in FIG. 21.

In the thirteenth embodiment, an insulation-coating process is performed on the shape memory element 41, and parylene is used as a coating agent. For example, an insulating film 55 is stacked on an outer circumference of the shape memory element 41. Furthermore, the contact spring 53 having a high coefficient of elasticity accommodates the shape memory element 41.

As shown in FIG. 21, the shape memory element 41 is allowed to be transformed by heating by energizing by an energizing unit (not shown in the diagram). At this time, an insulating film 55 is formed on the outer circumference of the shape memory element 41 in an area from a position overlapping with the bias-applying coil spring 61 in the radial direction, up to the caulking for fixing 52 which is fixed to the one end of the contact spring 53. Therefore, the shape memory element 41 and the contact spring 53 are not connected electrically. Accordingly, at the time of energizing, the shape memory element 41 is not affected electrically by the contact spring 53 or by the shape memory element 41, and it is possible to have an efficient driving.

The insulating film 55 formed by the insulation-coating process is a very thin film having a film thickness normally of several tens of microns (μm). Consequently, an inner diameter of the contact spring 53 may be bigger than an outer diameter of the shape memory element 41 by several tens of microns (μm). Therefore, it is possible to make small an overall outer diameter of a structure formed by the shape memory element 41, the insulating film 55, and the contact spring 53.

Moreover, by letting the contact spring 53 to be of a metallic material, it is possible to improve the heat radiation effect. Accordingly, it is possible to have a stable driving.

The protecting spring 54 and the contact spring 53 correspond to a hollow cable member which has a high coefficient of elasticity.

The present invention is not restricted to the endoscope, and can be provided to a driving mechanism of an optical device and an imaging device used in optical equipments such as a microscope. Moreover, the present invention can have various modified embodiments in a scope which fall within the basic teachings thereof.

Thus, the endoscope apparatus according to the present invention is useful for performing focusing, without making a diameter of an endoscope front end section thick.

According to the present invention, there is shown an effect that it is possible to provide an endoscope apparatus which is capable of performing the focusing by using a shape memory alloy, and of increasing an amount of change in relative positions of an imaging device and an optical device for the focusing, without increasing the diameter of the endoscope front end section.

What is claimed is:

1. An endoscope apparatus comprising:
a front end section, which is rigid, including an optical mechanism having a movable section; and
a flexible tube which has a bent portion, wherein
one end of a tube member which can be bent, is fixed to a lens barrel which holds the optical mechanism and
the tube member is extended in a longitudinal direction of the flexible tube which is included in the endoscope apparatus, and
at least a part of a shape memory element is accommodated inside the tube member, and
one end of the shape memory element is fixed to an end of the tube member which is not fixed to the lens barrel, and
the other end of the shape memory element is mechanically connected to the movable section of the optical mechanism and
relative positions of the movable section of the optical mechanism and the end of the tube member which is fixed to the lens barrel, are changed by expansion and contraction of the shape memory element.

2. The endoscope apparatus according to claim 1, wherein a bias-applying elastic body is disposed alongside the lens barrel such that a force is exerted in a reverse direction of changing the relative positions of the movable section of the optical mechanism and the end of the tube member which is fixed to the lens barrel, by a change in a length of the movable section of the optical mechanism by a phase transition of the shape memory element.

3. The endoscope apparatus according to claim 2, wherein a buffering elastic body which exerts on the end of the tube member which fixes the end of the shape memory element, a force in a reverse direction of a force generated at a time of change in the length by the phase transition of the shape memory element, is installed.

4. The endoscope apparatus according to claim 3, wherein a spring constant of the buffering elastic body is greater than a spring constant of the bias-applying elastic body.

5. The endoscope apparatus according to claim 4, wherein the buffering elastic body is disposed in the front end section.

6. The endoscope apparatus according to claim 4, wherein the buffering elastic body and the shape memory element are connected electrically.

7. The endoscope apparatus according to claim 4, wherein
an axial direction of the buffering elastic body and an axial direction of the bias-applying elastic body are parallel, and
at least a part of the buffering elastic body and a part of the bias-applying elastic body overlap by projecting in a vertical direction from the axial direction of the buffering elastic body.

8. The endoscope apparatus according to claim 2, wherein
one end of the shape memory element is fixed to the end of the tube member which is not fixed to the lens barrel, and
the other end of the shape memory element is mechanically connected to the movable section of the optical mechanism via a buffering elastic body, and
the relative positions of the movable section of the optical mechanism and the end of the tube member which is fixed to the lens barrel, are changed by expansion and contraction of the shape memory element, and
excessive expansion and contraction of the shape memory element, beyond the change in the relative position, is absorbed by expansion and contraction of the buffering elastic body.

9. The endoscope apparatus according to claim 8, wherein a spring constant of the buffering elastic body is greater than a spring constant of the bias-applying elastic body.

10. The endoscope apparatus according to claim 9, wherein the buffering elastic body is disposed in the front end section.

11. The endoscope apparatus according to claim 9, wherein the buffering elastic body and the shape memory element are connected electrically.

12. The endoscope apparatus according to claim 9, wherein
an axial direction of the buffering elastic body and an axial direction of the bias-applying elastic body are parallel, and
at least a part of the buffering elastic body and a part of the bias-applying elastic body overlap by projecting in a vertical direction from the axial direction of the buffering elastic body.

13. The endoscope apparatus according to claim 1, wherein
one end of the shape memory element is mechanically connected to the movable section of the optical mechanism via a connecting section, and
the movable section has a groove, and
the connecting portion is connected to the groove of the movable section via a gap between the connecting section and the groove.

14. The endoscope apparatus according to claim 1, wherein a stopper for limiting a range of movement of the movable section of the optical mechanism is installed on the lens barrel.

15. The endoscope apparatus according to claim 1, wherein the shape memory element is connected upon bending at a portion at which the shape memory element is mechanically connected to the movable section of the optical mechanism which includes the movable section.

16. The endoscope apparatus according to claim 1, wherein the tube member is non-conductive.

17. The endoscope apparatus according to claim 1, wherein
the tube member is accommodated in a hollow cable member which has a high coefficient of elasticity, and
one end of the hollow cable member having the high coefficient of elasticity, on a side of the tube member which is not fixed to the lens barrel, and the shape memory element, are fixed.

18. The endoscope apparatus according to claim 17, wherein the hollow cable member having the high coefficient of elasticity is a contact spring or a cable which includes a plurality of wires.

19. The endoscope apparatus according to claim 17, wherein
one end of the shape memory element is fixed by one end of the tube member, and
the other end of the tube member is not fixed to the lens barrel, and
in the hollow cable member having the high coefficient of elasticity, one end of the hollow cable member having the high coefficient of elasticity, and one end of the shape memory element are fixed, and the other end of the hollow cable member having the high efficient of elasticity is fixed to the lens barrel, and a force is exerted in a reverse direction of a force which is generated when a length is changed due to phase transition of the shape memory element, and a length is changed in the same direction as the direction of change in length by the phase transition of the shape memory element.

20. The endoscope apparatus according to claim 1, wherein the tube member is thermally connected to a pipe conduit of an endoscope.

21. The endoscope apparatus according to claim 20, wherein the pipe conduit is one of a gas pipe conduit and a water pipe conduit.

22. The endoscope apparatus according to claim 1, wherein
the optical mechanism includes an imaging device, and
not less than half a length of the shape memory element is disposed distally of the imaging device in the direction of the flexible tube.

23. The endoscope apparatus according to claim 1, wherein the movable section of the optical mechanism is an imaging device.

24. An endoscope apparatus comprising:
a front end section, which is rigid, including an optical mechanism having a movable section; and
a flexible tube which has a bent portion; wherein
one end of a hollow cable member which has a high coefficient of elasticity and which can be bent, is fixed to a lens barrel which holds the optical mechanism and
the hollow cable member is extended in a longitudinal direction of the flexible tube of the endoscope apparatus, and
at least a part of a shape memory element is accommodated inside the hollow cable member, and
one end of the shape memory element is fixed to an end of the hollow cable member which is not fixed to the lens barrel, and
the other end of the shape memory element is mechanically connected to the movable section of the optical mechanism; and
an energizing means which energizes and heats up the shape memory element, wherein
an insulation-coating process is performed on a portion other than a portion at which the shape memory element is electrically connected to the energizing means, and
a temperature of the shape memory element is changed by heating by the energizing means, and
relative positions of the movable section of the optical mechanism and the end of the hollow cable member which is fixed to the lens barrel, are changed by expansion and contraction based on a temperature change of the shape memory element.

25. The endoscope apparatus according to claim 24, wherein a bias-applying elastic body is disposed in the lens barrel such that a force is exerted in a reverse direction of changing the relative positions of the movable section of the optical mechanism which has the movable section, and the end of the hollow cable member which is fixed to the lens barrel, by a change in a length of the movable section of the optical mechanism by a phase transition of the shape memory element.

26. The endoscope apparatus according to claim 24, wherein
one end of the shape memory element is mechanically connected to the movable section of the optical mechanism via a connecting section, and
the movable section has a groove, and
the connecting section is connected to the grove of the movable section via a gap between the connecting section and the groove.

27. The endoscope apparatus according to claim 24, wherein a stopper for limiting a range of movement of the movable section of the optical mechanism is installed on the lens barrel.

28. The endoscope apparatus according to claim 24, wherein the shape memory element is connected upon bending at a portion at which the shape memory element is mechanically connected to the movable section of the optical mechanism which includes the movable section.

29. The endoscope apparatus according to claim 24, wherein the hollow cable member is a contact spring or a cable which includes a plurality of wires.

30. The endoscope apparatus according to claim 24, wherein
a force in a reverse direction of a force generated at a time of change in the length by the phase transition of the shape memory element, is exerted on the hollow cable member, and
a length is changed in a direction same as the change in the length by the phase transition of the shape memory element.

31. The endoscope apparatus according to claim 24, wherein the hollow cable member is thermally connected to a pipe conduit of an endoscope.

32. The endoscope apparatus according to claim 31, wherein the pipe conduit is one of a gas pipe conduit and a water pipe conduit.

33. The endoscope apparatus according to claim 24, wherein the optical mechanism includes an imaging device, and not less than half a length of the shape memory element is disposed toward the flexible tube, farther than a position of the imaging device.

34. The endoscope apparatus according to claim 24, wherein the movable section of the optical mechanism is an imaging device.

35. The endoscope apparatus according to claim 24, wherein a material in the insulation-coating process is parylene.

* * * * *